(12) United States Patent
O'Keefe et al.

(10) Patent No.: US 12,171,721 B2
(45) Date of Patent: Dec. 24, 2024

(54) CONNECTORS FOR INFUSION PUMP FEEDING SETS

(71) Applicant: VESCO MEDICAL LLC, Columbus, OH (US)

(72) Inventors: Christopher O'Keefe, Columbus, OH (US); Joseph Ryan, Phoenix, AZ (US); Rachel Kunzweiler, Columbus, OH (US); Aaron Szabo, Columbus, OH (US)

(73) Assignee: VESCO MEDICAL LLC, Columbus, OH (US)

( * ) Notice: Subject to any disclaimer, the term of this patent is extended or adjusted under 35 U.S.C. 154(b) by 649 days.

(21) Appl. No.: 17/377,567

(22) Filed: Jul. 16, 2021

(65) Prior Publication Data

US 2021/0353507 A1    Nov. 18, 2021

Related U.S. Application Data

(62) Division of application No. 16/135,080, filed on Sep. 19, 2018, now Pat. No. 11,213,460.

(51) Int. Cl.
*A61J 15/00* (2006.01)
*A61M 39/10* (2006.01)

(52) U.S. Cl.
CPC ....... *A61J 15/0053* (2013.01); *A61J 15/0015* (2013.01); *A61M 39/10* (2013.01); *A61M 2202/0482* (2013.01)

(58) Field of Classification Search
CPC .............. A61M 39/288; A61M 5/14232; A61J 15/0076; F04B 43/12; F04B 43/1261; F04B 43/0072
See application file for complete search history.

(56) References Cited

U.S. PATENT DOCUMENTS

| | | | | |
|---|---|---|---|---|
| 4,354,660 A | * | 10/1982 | Stupar | A61M 39/288 422/938 |
| 8,425,470 B2 | * | 4/2013 | Beck | A61M 39/24 137/853 |

FOREIGN PATENT DOCUMENTS

WO    2017218927 A1    12/2017

OTHER PUBLICATIONS

Extended European Search Report dated Aug. 12, 2022 in related European Application No. 19861721.9 filed Sep. 17, 2019 (9 pages).

* cited by examiner

*Primary Examiner* — Laura A Bouchelle
(74) *Attorney, Agent, or Firm* — Ronald J. Richter; Nesbitt IP LLC

(57) ABSTRACT

Improved feeding set connectors and cassettes are disclosed for use with peristaltic infusion pumps for safely delivering enteral nutritional fluids to a patient. The connectors provide an easy to use "pump-to-set" integration or "keying" system for specific reusable infusion pumps and their matching feeding sets, and can be utilized by medical professionals having various skill levels. The inventive feeding set cassettes can prevent accidental free flow of enteral fluids into a patient, even upon inadvertent release of the connector from the pumping mechanism.

3 Claims, 9 Drawing Sheets

CONNECTORS FOR INFUSION PUMP FEEDING SETS

CROSS-REFERENCE TO RELATED APPLICATION

The present application is a divisional of U.S. patent application Ser. No. 16/135,080 filed Sep. 19, 2018, the disclosure of which is incorporated by reference in its entirety.

FIELD OF THE INVENTION

The present invention relates generally to delivery of enteral nutritional fluids to a patient, and in particular to safe and reliable loading of enteral nutrition feeding sets to matching peristaltic infusion pumps to prevent free flow of fluids into the patient.

BACKGROUND OF THE INVENTION

Enteral nutrition generally refers to a method of feeding that uses the gastrointestinal (GI) tract to deliver part or all of a person's daily caloric requirements. While enteral nutrition can include a normal oral diet and oral administration of liquid supplements and medications, it typically refers to delivery of some or all of a patient's daily caloric requirements by use of a tube (i.e. tube feeding). Enteral nutritional products are typically in the form of a relatively thick, flowable liquid or fluid, and many types are available for a variety of replacement and supplemental feeding requirements. In contrast, parenteral nutrition and total parenteral nutrition (TPN) refer to the intravenous delivery of some or all of the daily caloric requirements. Many hospitalized patients are given dextrose or amino acids by this method.

Enteral tube feeding is the preferred method of feeding when patients are unable to consume enough calories on their own, yet have a functional GI tract. Enteral access devices include many different types of feeding tubes placed directly into the GI tract, including orogastric and nasogastric tubes which are inserted through the mouth or nose, as well as percutaneous endoscopic gastrostomy (PEG, G-tubes) and jejunostomy tubes (J-tubes) which are inserted through the skin via a small incision through the abdominal wall. For example, stroke patients suffering from dysphagia may require enteral tube feeding both early in their recovery via a nasogastric tube, and permanently if necessary via a PEG tube.

Motor-driven peristaltic infusion pumps are commonplace for both enteral and parenteral applications, and provide controlled delivery of liquid nutrition, fluids and medications for various purposes. In a common arrangement, an infusion pump includes a motorized pumping mechanism which is connected to various components and/or accessories for transferring the fluid or liquid nutritional product from a container (e.g., a bottle or a collapsible bag) into the patient. The container is typically provided in combination with compressible tubing, as well as other connections and fitments for accessing the patient's GI tract. Enteral tubing delivers fluids having a much thicker consistency than intravenous fluids, and so typically has a larger internal diameter compared to parenteral tubing. All of these components (e.g., container, tubing and connectors) are often collectively referred to as a feeding set. The feeding set is typically single-use and disposable, while the infusion pump itself is typically reused many times.

Both rotary and linear peristaltic infusion pumps are well-known and commonly used for enteral feeding. The pumping mechanism for a rotary peristaltic pump as known in the art typically includes a motor-driven rotor fitted with a set of circumferentially spaced rollers, cams or fingers which during operation compress a segment of the feeding set tubing. The feeding set tubing is typically wrapped or otherwise stretched or tensioned around the rotor, and as the rotor turns the rollers are sequentially brought into contact with the tubing to cause the fluid to peristaltically flow through the tubing and into the patient's GI tract at a desired volumetric rate. In contrast to rotary pumping mechanisms, the pumping mechanism for a linear peristaltic pump uses a plurality of mechanical fingers or cams which extend and retract in a wave format to compress the pump tubing. A rotor typically is used to operate the movement of the fingers, which translate the rotational motion of the rotor into a linear peristalsis. When placed alongside an elastic conduit or feeding tube segment, the fingers can reversibly compress and occlude the tubing in this wave format so as to cause the fluid to peristaltically flow through the tube at a desired volumetric rate.

Whether the pumping mechanism for a peristaltic infusion pump is rotary or linear in design, as each roller revolves around the rotor (in a rotary pump), or as each finger moves to its extended position (in a linear pump), the pumping mechanism makes contact with a portion of the tubing, compressing it to form an occlusion. Free flow of fluid is therefore restricted by the pressure of the pump rollers/fingers synchronously closing off the tubing. Each occlusion is advanced along the tubing and then released, so that a specific volume of fluid is advanced between successive occlusions through the tubing by the pumping mechanism. The infusion pump can therefore deliver a predetermined amount of fluid to the patient over a period of time.

Despite improvements over the years, manufacturers and users of both rotary and linear peristaltic infusion pumps have continued to experience a number of difficulties and challenges. For example, with many of the commercially available peristaltic pumps it is problematic that the feeding set may be improperly mounted to the infusion pump. Indeed, many prior art infusion pump designs make it possible for unintended disconnection of the pump tubing from the rollers. For example, the patient's movements in their bed may inadvertently pull the feeding set tubing from the pump, which can release the restriction of flow provided by compression the tubing by the pumping mechanism, leaving only the force of gravity to control the flow of the enteral fluid into the patient. This situation is commonly referred to as "free flow", and occurs when the pumping mechanism's rollers, cams and/or fingers are not able to properly compress the tubing to restrict flow into the patient. Such uncontrolled flow can result in a large volume of feeding fluid being delivered into a patient over a very short period of time, which can lead to serious medical problems including aspiration (food entering the lungs), pneumonia, high blood sugar, nausea, vomiting, and sometimes death in more frail patients due to sudden cardiac arrest.

Numerous devices have been developed in an attempt to prevent such free flow conditions. These devices are typically manually operated clamps or cassettes, with some form of automatic flow control mechanism. However, such devices are typically complex in design and can add significantly to the overall cost of the infusion set, while providing only marginal protection against free flow. Furthermore, proper use of these devices can be complicated, making it difficult for medical personnel to properly operate them. Indeed, inadvertent free flow errors have occurred in diverse clinical settings, causing serious patient injuries and deaths. Despite advances in many areas of infusion pump design, disconnections leading to free flow continue to create dangerous medical situations.

In light of the above, it is apparent that there is a need in the art for an improved means to safely deliver enteral nutritional fluids to a patient. It would thus be beneficial to provide a device and method for preventing inadvertent free flow of enteral fluids into a patient. It would likewise be advantageous to provide a cassette for an enteral infusion pump that can be utilized by medical professionals and other users having various skill levels. It would also be beneficial to replace complex infusion pump connection features with intuitively easy-to-use features which reduce user confusion, decrease manufacturing costs and improve safety.

SUMMARY OF THE INVENTION

Accordingly, the present invention provides improved means for connecting a feeding set to a peristaltic infusion pump. The inventive connectors and cassettes can be quickly and easily connected to the infusion pump while reliably ensuring that free flow of fluids will not occur, even upon inadvertent release of the feeding set tubing from the pump.

A first aspect of the invention provides a cassette for providing an interface between a feeding set and a peristaltic infusion pump for delivery of an enteral nutritional fluid to a patient, the cassette comprising: (a) a pump tubing segment for engaging a pumping mechanism located within a receiving portion of a peristaltic infusion pump, the pump tubing segment comprising an anti-flow mechanism for preventing free flow of enteral nutritional fluid through the pump tubing segment, wherein the anti-flow mechanism causes an obstruction to flow when the pump tubing segment is not engaged with the pumping mechanism; and (b) a connector for connecting to the infusion pump, wherein connection of the connector with the infusion pump aligns the pump tubing segment with the pumping mechanism and locks the cassette in place within the infusion pump, and wherein engagement of the pump tubing segment with the pumping mechanism overcomes the anti-flow mechanism of the pump tubing.

A second aspect of the invention provides a cassette for loading a nutritional feeding set onto a peristaltic infusion pump, the cassette comprising: (a) a pump tubing segment for engagement with a motor-driven pumping mechanism located within a receiving portion of a peristaltic infusion pump, the pump tubing segment including: (i) an anti-flow mechanism for preventing free flow of fluid through the pump tubing segment, wherein the anti-flow mechanism causes an obstruction to flow when the pump tubing segment is not engaged with the pumping mechanism; and (ii) a pair of free ends; and (b) a connector for connecting to the receiving portion of the infusion pump, the connector including: (i) a first mating member for reversibly connecting to a second mating member located in the receiving portion of the infusion pump, wherein connection of the first mating member with the second mating member aligns the pump tubing segment with the pumping mechanism and locks the cassette in place within the receiving portion; (ii) a first set of attachment structures for connecting inflow tubing and outflow tubing of a nutritional feeding set to the connector; and (ii) a second set of attachment structures for connecting the free ends of the pump tubing segment to the connector, wherein the attachment structures are hollow and fluidly connect the inflow tubing and the outflow tubing to the pump tubing segment.

A third aspect of the invention provides a method for loading a nutritional feeding set onto a peristaltic infusion pump, the method comprising: (a) providing a peristaltic infusion pump, the infusion pump comprising: (i) a housing, the housing including a receiving portion; and (ii) a motor-driven pumping mechanism within the receiving portion; (b) providing a cassette configured to load a nutritional feeding set onto the infusion pump, the cassette comprising: (i) a pump tubing segment for engagement with the pumping mechanism, the pump tubing segment including an anti-flow mechanism for preventing free flow of fluid through the pump tubing segment when the pump tubing segment is not engaged with the pumping mechanism; and (ii) a connector for connecting to the receiving portion of the infusion pump, the connector including a first mating member for reversibly connecting to a second mating member located in the receiving portion of the infusion pump, wherein connection of the first mating member with the second mating member aligns the pump tubing segment with the pumping mechanism and locks the cassette in place within the receiving portion; (c) inserting the cassette within the receiving portion of the pump housing; (d) connecting the first mating member with the second mating member; (e) engaging the pump tubing segment with the pumping mechanism to overcome the anti-flow mechanism of the pump tubing; and (f) actuating the pumping mechanism to cause controlled flow of nutritional fluid through the feeding set.

In all of the embodiments described herein an optical reader can be incorporated into the infusion pump to verify that its matching feeding set tubing has been properly loaded. The nature and advantages of the present invention will be more fully appreciated after reviewing the accompanying drawings, detailed description, and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

Figure 1:
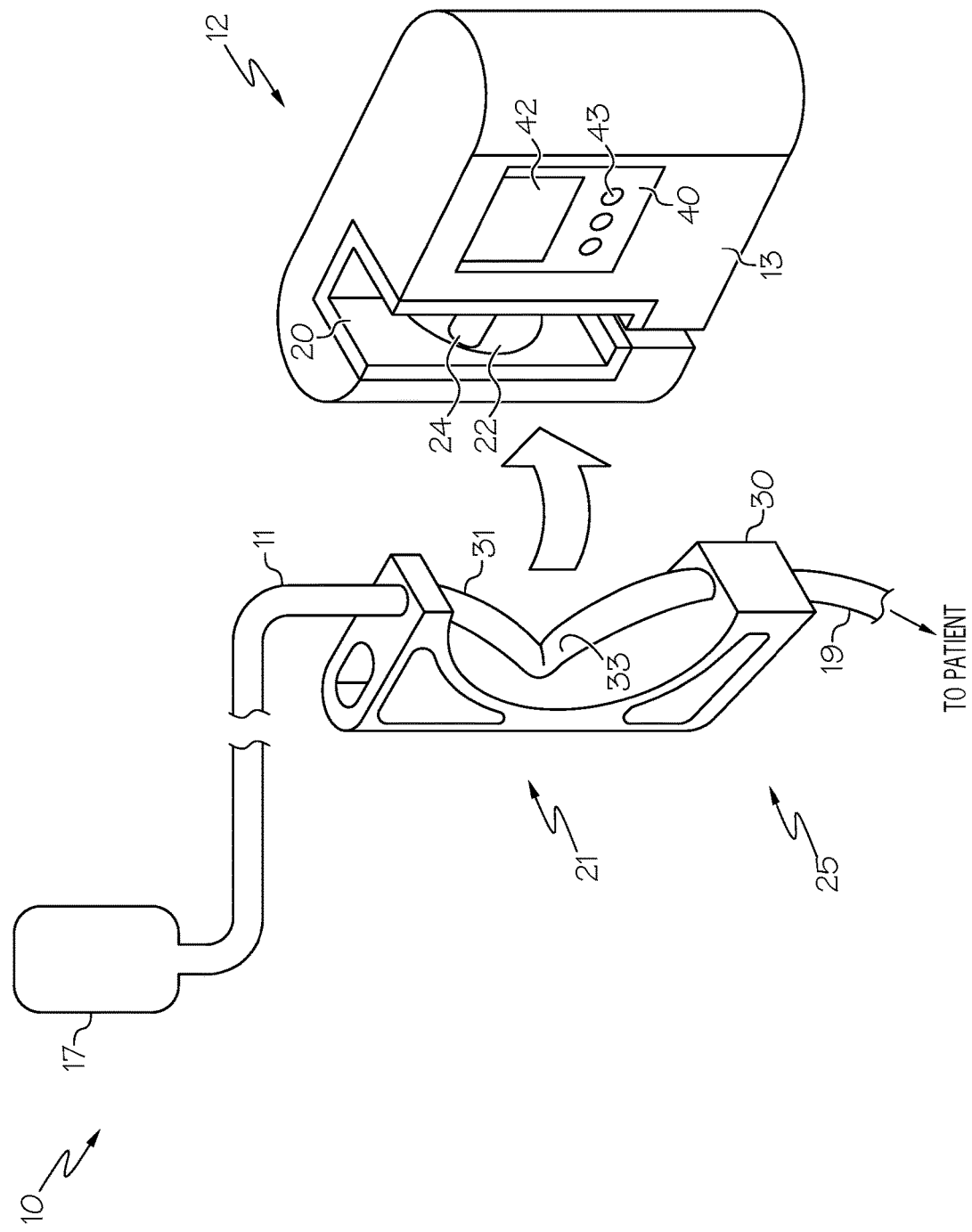
FIG. 1 is an elevated perspective view of a peristaltic infusion pump and a "pre-kinked" cassette embodiment according to the principles of the invention.

Below is disclosed a plurality of embodiments of infusion pump connectors and cassettes, as defined herein, for connecting an enteral nutritional fluid feeding set to a peristaltic infusion pump. The cassettes allow the feeding set to be quickly connected to the infusion pump while reliably ensuring that inadvertent free flow of fluids will not occur when the feeding set tubing is not engaged by the infusion pump's rollers.

As used herein, the terms "connector(s)", "connection(s)" and "connector device(s)" mean a device for reversibly connecting a peristaltic infusion pump to a feeding set. A connector is typically one element of a cassette, as defined herein, and can provide a simple "infusion pump-to-feeding set" integration or "keying" system for connecting a single use feeding set to a matching reusable infusion pump, ensuring proper operation of both.

The term "cassette" as used herein means a portion of a feeding set, specifically, a connector in combination with a pump tubing segment, as defined herein. In use, the connector portion of a cassette can be locked into a receiving portion of a peristaltic infusion pump housing, which aligns the pump tubing segment for engagement with the pumping mechanism.

The terms "engage", "engaged", "engaged with", "engaged by" "engagement", or "engagement with" as used herein refer to the relationship between the pump tubing segment and the pumping mechanism as defined herein, and specifically mean stretching engagement or external tensioning of the pump tubing segment by the pumping mechanism. For example, recitation in the claims of "a pump tubing segment for engagement with a pumping mechanism" means that the pump tubing segment is caused to be stretched or placed under external tension by the pumping mechanism; disengagement means removal of this tension or stretching.

The phrase "feeding set" as used herein is a collective term which includes a container (having a particular nutritional fluid), feeding set tubing (as defined below), and a cassette (as defined above). A feeding set may also be referred to in the art as a "fluid delivery set", "infusion set", "feed set" or "pump set".

The phrase "feeding set tubing" as used herein is a collective term which when used herein includes inflow tubing, outflow tubing, and a pump tubing segment (as each are defined herein). The feeding set tubing is typically a compressible, single-use and disposable type of tubing, but it may also be reusable.

The phrase "inflow tubing" as used herein means a segment of the feeding set tubing which connects the container to the proximal end of the pump tubing segment.

The phrase "motor-driven pumping mechanism" or "pumping mechanism" as used herein means the pumping machinery for a peristaltic infusion pump, which can be either rotary or linear in design. If pertaining to a rotary pump, the pumping mechanism can be an array of spaced apart and circumferentially mounted rollers, cams or fingers which are mounted to and rotate around a motor-driven rotor to sequentially make contact with, compress and occlude a segment of the feeding set tubing. If pertaining to a linear pump, the pumping mechanism can be an array of rollers, cams or fingers which are moved by a motor-driven rotor to an extended position in a wave format to sequentially make contact with, compress and occlude a segment of the feeding set tubing. Whether the pumping mechanism for a peristaltic infusion pump is rotary or linear in design, in operation the free flow of fluid is restricted by the pressure of the pump rollers/fingers synchronously closing off the tubing.

The phrase "outflow tubing" as used herein means a segment of the feeding set tubing which connects the distal end of the pump tubing segment to the patient.

The phrases "pump tubing" and "pump tubing segment" as used herein refer to a piece or segment of the feeding set tubing that is coupled with a connector to form a cassette. The pump tubing segment engages, i.e. is stretched or externally tensioned by the motor-driven pumping mechanism of a peristaltic infusion pump. The pump tubing segment includes a proximal end which typically connects to the inflow tubing, and a distal end which typically connects to the outflow tubing of the feeding set.

As known in the art, a "peristaltic infusion pump" or "infusion pump" typically includes a mechanical pump having a housing for receiving tubing of a feeding set, and a motor-driven pumping mechanism (as defined herein) mounted in the housing for driving nutritional fluid through the feeding set.

A preferred embodiment of a cassette for a nutritional fluid delivery system 10 according to the present invention is shown in FIGS. 1-4. Looking at FIG. 1, a "pre-kinked" cassette 21 is intended to assist in loading a feeding set 25 onto an infusion pump 12, for controlled delivery of nutritional fluid to a patient. The feeding set 25 includes inflow tubing 11 and outflow tubing 19, together with a segment of pump tubing 31, and the three tubing segments 11, 31, 19 complete a fluidic pathway between a container or bag 17 of nutritional fluid and the patient. A receiving portion 20 within the front housing 13 of a peristaltic infusion pump 12 can provide access to a pumping mechanism, here in the form of a motor-driven rotor 22 mounted on a rotatable shaft.

According to the present invention, a user typically mounts the cassette 21 to a corresponding infusion pump 12 and primes the feeding set 25 with the prescribed nutritional fluid stored inside the container 17. Thereafter the loaded feeding set can be connected to the patient and the infusion pump can be actuated by a medical professional or other user to effect safe and controlled delivery of the proper nutritional fluid to the patient.

The housing 13 of the infusion pump 12 typically includes a user interface 40 with a display screen 42 capable of displaying information about the status and operation of the pump. The user interface 40 can further include buttons 43 for use with the display screen 42 to facilitate exchanging information between the pump 12 and the user. Various user interfaces may be implemented as known in the art for displaying and receiving information.

The cassette 21 serves as a "keyed" interface device for connecting the feeding set 25 to the infusion pump 12, and includes a connector 30 and a segment of kinked pump tubing 31. The connector 30 is designed to hold a predetermined length or segment of pump tubing 31, which is seated within the connector 30 and includes an anti-flow mechanism in the form of a "pre-set kink" 33. This pre-set kink 33 is manufactured into the pump tubing and, when not stretched or placed under external tension around the rotor 22, presents an obstruction to free flow of fluid through the pump tubing segment 31.

Figure 2:
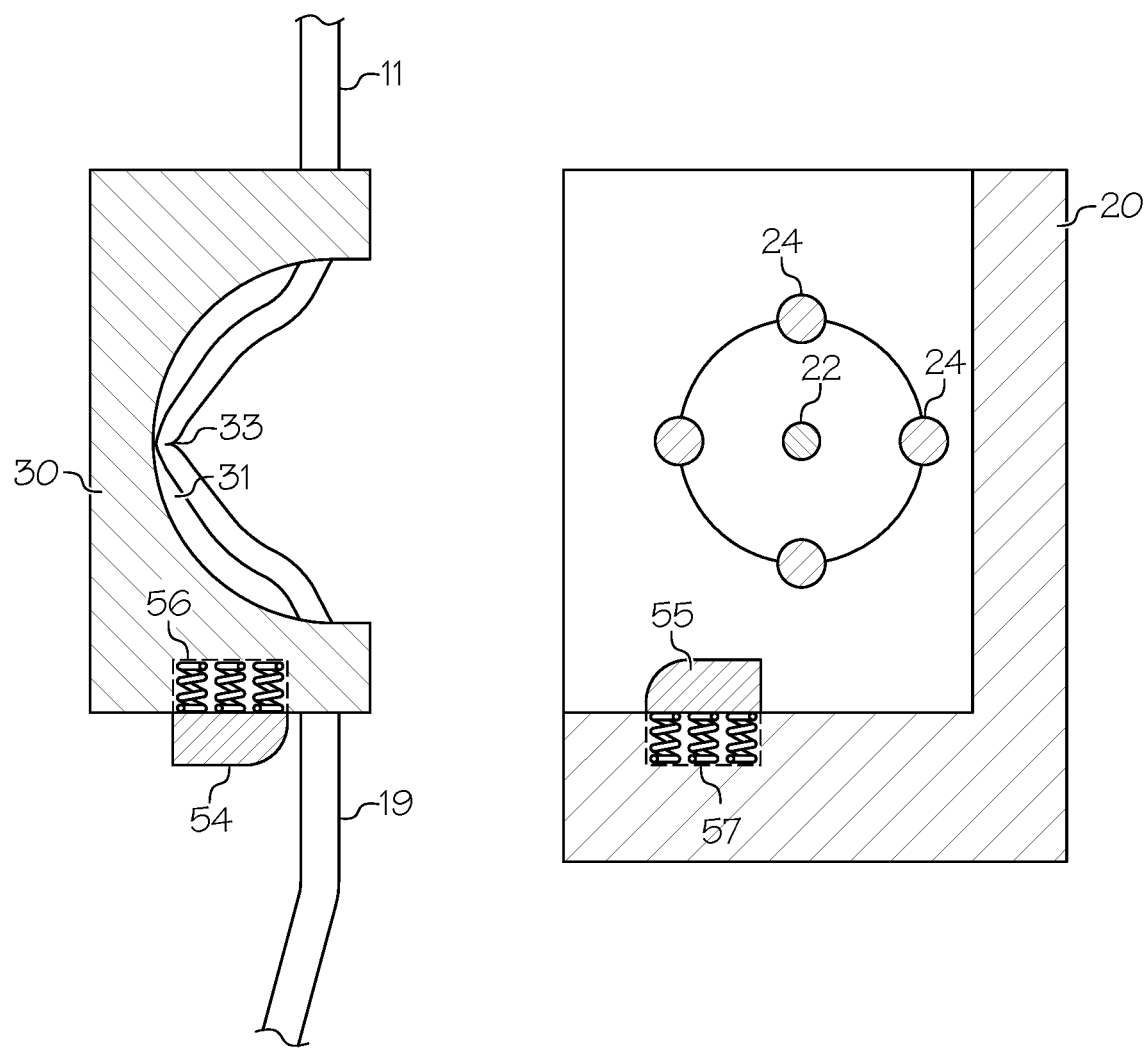
FIG. 2 is a schematic cross-sectional view of the infusion pump and cassette of FIG. 1 prior to insertion into the infusion pump's receiving portion.
Figure 4:
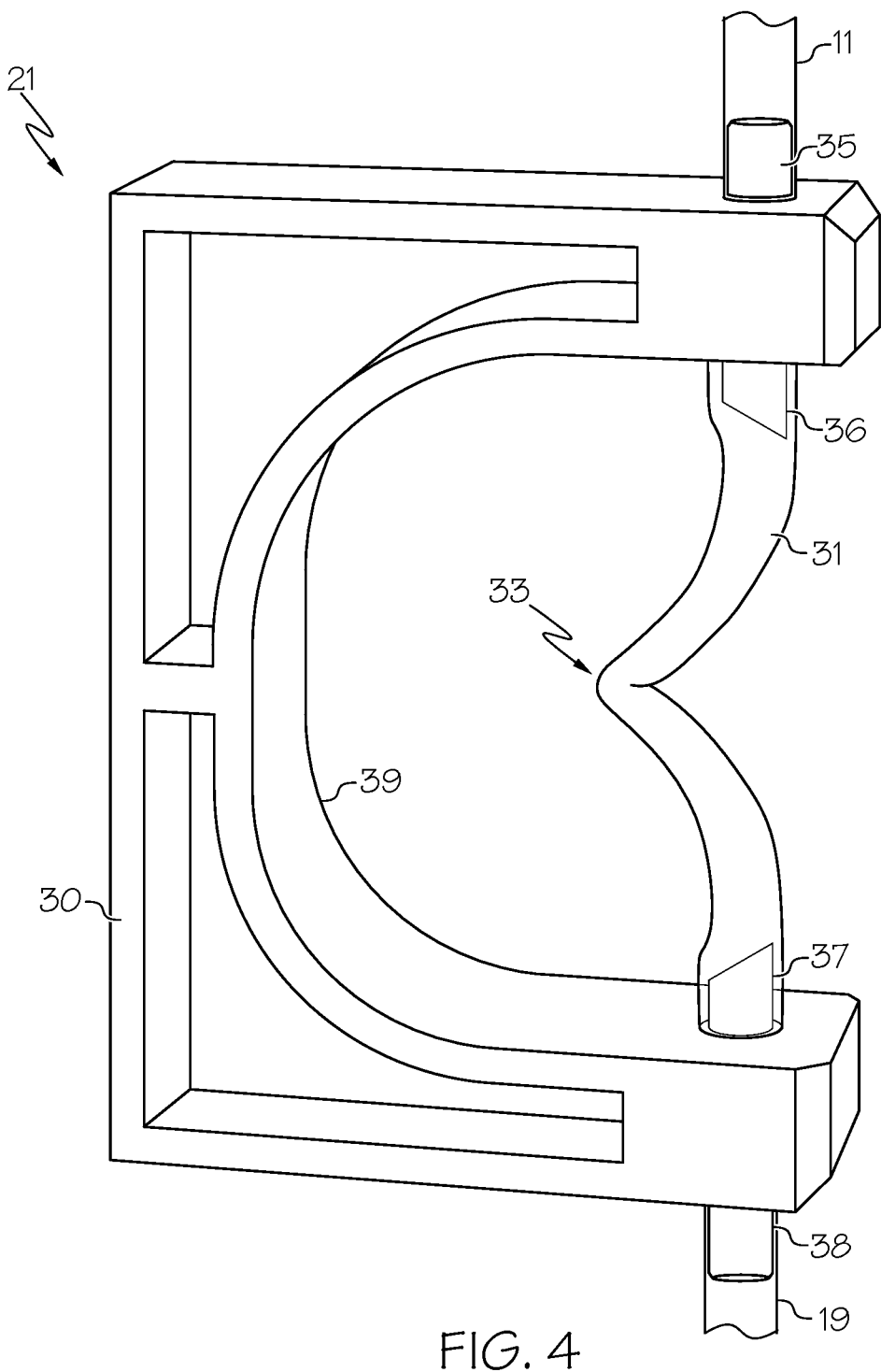
FIG. 4 is a close-up perspective view of the cassette of FIG. 1.

As can be appreciated from viewing FIGS. 1, 2 and 4, the pre-set kink or anti-flow mechanism 33 manufactured into the pump tubing prevents free flow of fluid when it is not stretched or placed under external tension around the pumping mechanism 22. As can be appreciated from viewing FIG.

3, the obstruction 33 is reversible and can be relieved when the pump tubing segment 31 is stretched or tensioned about the rotor 22. Unlike long, hanging segments of tubing which are typically caused to kink by prior art pinch valves, the pre-set kink 33 is located in a tubing segment 31 which does not hang freely for access by a user; rather, the kinked pump tubing segment 31 is protected within the connector and is intended to be reversibly engaged (i.e. tensioned about) and disengaged with the pumping mechanism 22.

As noted above, the housing 13 of the infusion pump 12 includes a receiving portion 20 in the form of a window or door. The recessed shape of the receiving portion 20 preferably matches the physical shape of the cassette 21, so that only a cartridge identical to the connector 30 of the pre-kinked cassette 21 can be locked into the receiving portion 20 of the pump 12. This advantageously decreases the chances of an inadvertent connection between incompatible products, and can ensure that only a particular brand of feeding set can be connected to a particular brand of infusion pump. For example, both the cassette's connector 30 and the pump's receiving portion 20 can include a mating member 54, 55, respectively (see FIGS. 2, 3 and 5), such that a specific cassette can be configured to reversibly connect to only a specific infusion pump, to ensure that the correct infusion pump is being used with the correct corresponding feeding set. As discussed below, an optical reader can also be incorporated into the infusion pump to read an imprinted item on the feeding set tubing (typically on the pump tubing segment). The optical reader can thus verify that a specific infusion pump has been properly loaded with a matching feeding set, so that the prescribed nutritional fluid can be properly and safely delivered.

In use, a medical professional can load the cassette 21 into the receiving portion 20 of the infusion pump by first aligning the cassette with the pumping mechanism 22 and then sliding, snapping, locking, mating, or otherwise reversibly connecting the mating member 54 of the connector 30 with the mating member 55 of the receiving portion. In the embodiment shown in FIGS. 1-4, proper alignment and insertion of the connector 30 within the receiving portion 20 allows the pump tubing 31 within the cassette 21 to be automatically tensioned or stretched around the rotor 22 of the infusion pump. In other embodiments, e.g. FIGS. 5-7, the pump tubing segment 31 must initially be tensioned manually about the pumping mechanism 22, such as by the user stretching the pump tubing around or over the pump rotor.

FIG. 2 illustrates the connector's mating member 54 extending from a recess 56. Mating member 54 can reversibly connect to the pump housing's mating member 55, which is seated in and extends from a recess 57 in the pump's receiving portion 20. The mating members 54, 55 can function in a manner that is known in the art. For example, the mating members 54, 55 can be configured to reversibly extend from spring-loaded recesses 56, 57 as illustrated in FIG. 2, such that proper insertion of the cassette by the user causes the mating members to push one another into their respective spring-loaded recesses. In one embodiment, the mating members can function much like a pen that a user clicks to extend and/or retract the writing element, initially "over centering" within their recesses and then locking back into place. To release the cassette, the user can then simply push down on the loaded cassette, causing the mating members to be expelled from their recesses. Removal of the cassette 21 from the pumping mechanism 22 will remove the tension in the pump tubing segment 31 and cause the pre-set kink 33 to form once again, once again causing an obstruction to the free flow of fluid. A similar type of retention means can include a snap-in feature as is known in the art, in which a push button (not shown) on the pump display can be pressed to release the cassette from the pump.

Each mating member 54, 55 can be shaped to easily slide onto and make contact with the other during initial insertion. In addition, each mating member may have a particular profile, e.g. a rectangular button, slot or pin having a hemispherical or concave shape, which can correspond to the other. In other embodiments (see, e.g., cassette 61 of FIG. 6), the cassette can be retained in the pump's receiving portion by a friction fit between the mating members. The mating members can have any shape and can be made of any suitable material, so long as they can function to reversibly load and secure the cassette to the infusion pump.

In addition to ensuring proper alignment and locking of the cassette 21 in place within the receiving portion 20, the mating member 55 of the pump housing 13 can also be associated with, or serve as, a micro-switch which must first be triggered or activated before the pumping mechanism 22 can be set in motion. Proper insertion of the cassette into the receiving portion of the pump housing can cause connection of the mating members 54, 55, which locks the cassette in place and also triggers the micro-switch 55, which then allows the pumping mechanism or rotor to be acuated.

Figure 3:
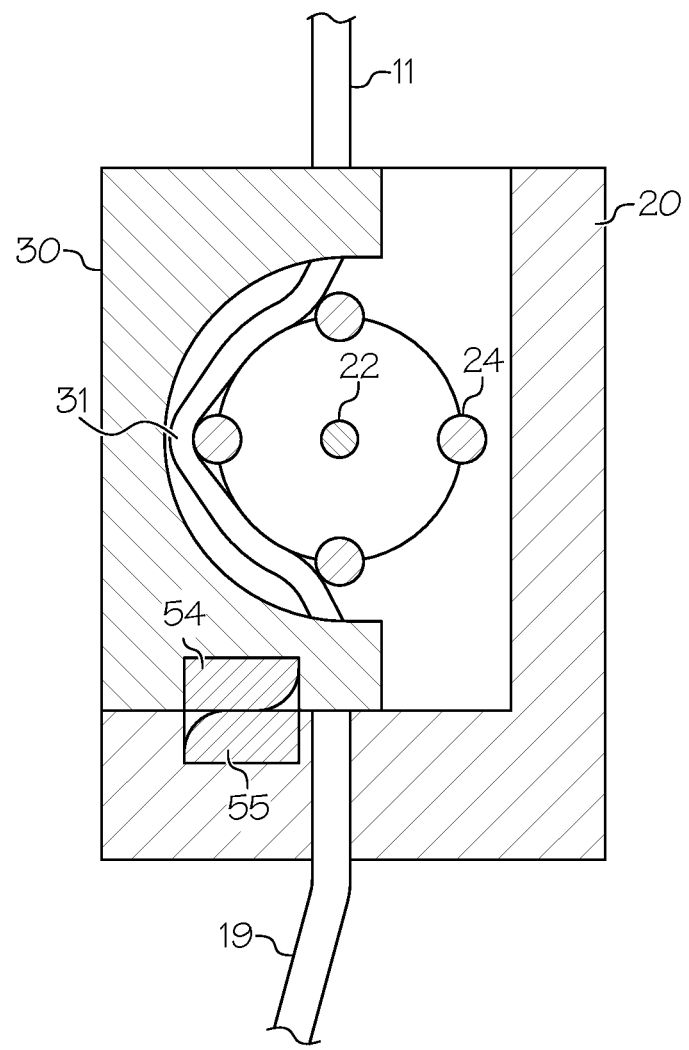
FIG. 3 is a schematic cross-sectional view of the infusion pump and cassette of FIG. 1 after insertion into the infusion pump's receiving portion.

As can be appreciated from viewing FIG. 3, loading the cassette 21 into the pump 12 stretches and relieves the obstruction to fluid flow in the kinked pump tubing 31, so that fluid can now be caused to flow through the pump tubing 31. The restriction of flow is now under the control of the pumping mechanism, i.e. rotor 22 and its circumferentially mounted rollers 24, such that controlled flow can be instituted when the motor-driven pump is actuated. More specifically, when the cassette 21, including the connector 30 and its associated kinked pump tubing segment 31 is locked into the receiving portion 20, the pre-set kink 33 engages and is tensioned around the rotor 22, stretching the kink 33 to overcome its anti-flow capabilities. The now un-kinked pump tubing 31 is engaged with the pump rotor 22 and its rollers 24, and the nutritional fluid in the container 17 can be delivered through the feeding set 25 in a controlled manner by activation of the infusion pump. Should the pump tubing 31 for some reason become disengaged from the pumping mechanism during use, either inadvertently or intentionally, the roller's tension on the pump tubing 31 would be released which will allow the pre-set kink 33 to return to a kinked position, once again preventing any free flow of fluid through the feeding set.

It is notable that cassette 21 of FIGS. 1-4 provides and also protects the connection between the feeding set 25 and the pumping mechanism 22. Specifically, while most infusion pumps have a separate door or cover for protecting the interface between the feeding set tubing and the pump, the inventive connector 30 serves as an insertable door/cover that also provides such an interface. Further, due to the kink 33 in the pump tubing 31, when the connector is not inserted into the pump receiving portion 20, the free flow of fluids through the feeding set 25 is prevented by the kink 33. In use, the connector can be quickly inserted into the pump 12 via the receiving portion 20, putting tension on the kink 33 and thus allowing mechanical fluid flow, and the pumping mechanism 22 can then be actuated to deliver nutritional fluid to the patient.

The pre-kinked cassette 21 embodiment of the invention is shown in more detail in FIG. 4. The pump tubing 31 is seated within an inner curve 39 of the connector 30, the shape of which substantially matches the physical curvature of the rotor 22, such that insertion of the connector 30 tensions the pump tubing 31 around the rotor. External attachment structures 35 and 38, located outside the opposing ends of the inner curve 39, can be included to provide facile and secure attachment of the inflow tubing 11 and outflow tubing 19, respectively. Internal attachment structures 36 and 37 located inside the opposing ends of the inner curve 39 can provide means to easily and securely connect the free ends of the pump tubing segment 31 to the connector 30. The attachment structures 35-38 are typically hollow, having substantially the same size and diameter as the tubing 11, 19, 31 they connect to. Further, attachment structures 35 and 36 are fluidly connected to one another by a pathway through the body of the connector, as are attachment structures 37 and 38. That is, their hollow structures pass through the opposing ends of the inner curve 39 of the connector 30, ensuring that inflow tubing 11 and outflow tubing 19 are fluidly connectable to one another via the pump tubing 31 of the cassette.

Depending on the desired feeding regime, the container 17 and tubing 11, 31, 19 of the feeding set 25 can be varied for different types of nutritional fluid. For example, the attachment structures 35-38 may connect only to a particularly sized tubing, e.g. tubing having a specific diameter and which is associated with a specific type or formula of nutritional fluid product. The flow rate may depend on the tubing resistance of a particular feeding set, and/or the consistency or viscosity of the fluid being delivered through the feeding set. The inventive cassette can therefore both advantageously reduce the likelihood of an inadvertent connection between incompatible products, and increase the likelihood of delivering nutritional fluid according to the intended delivery protocol.

Figure 5A:
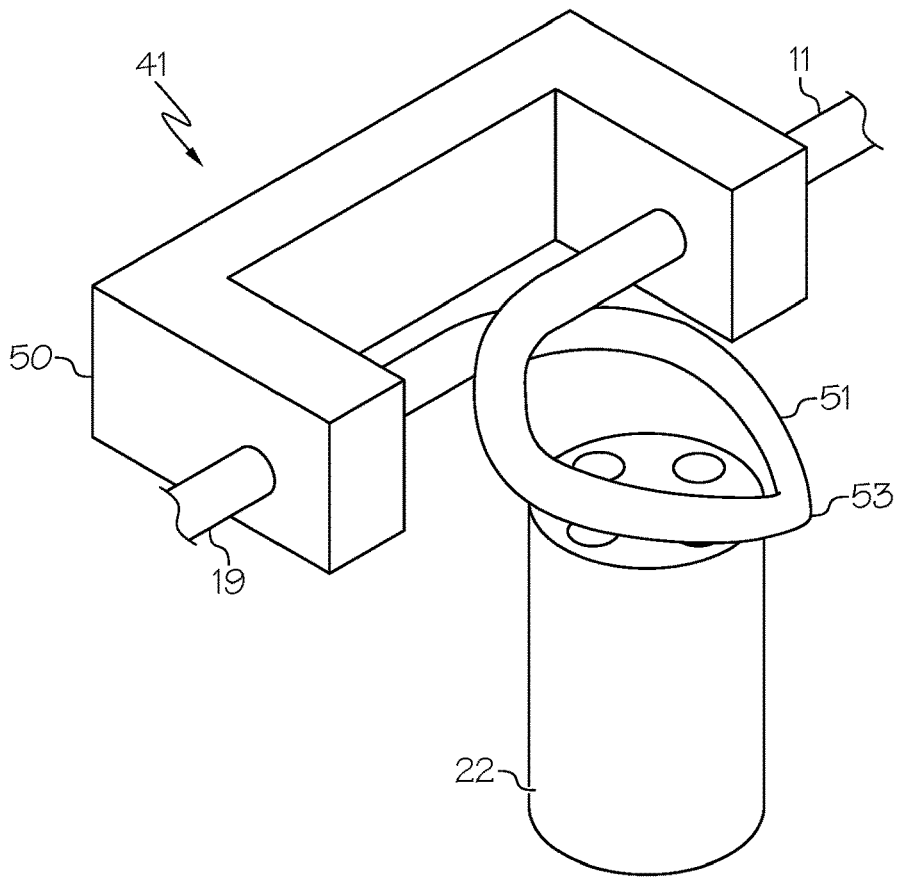
FIGS. 5A and 5B are schematic views of a pre-kinked "loop" cassette embodiment according to the present invention.
Figure 5B:
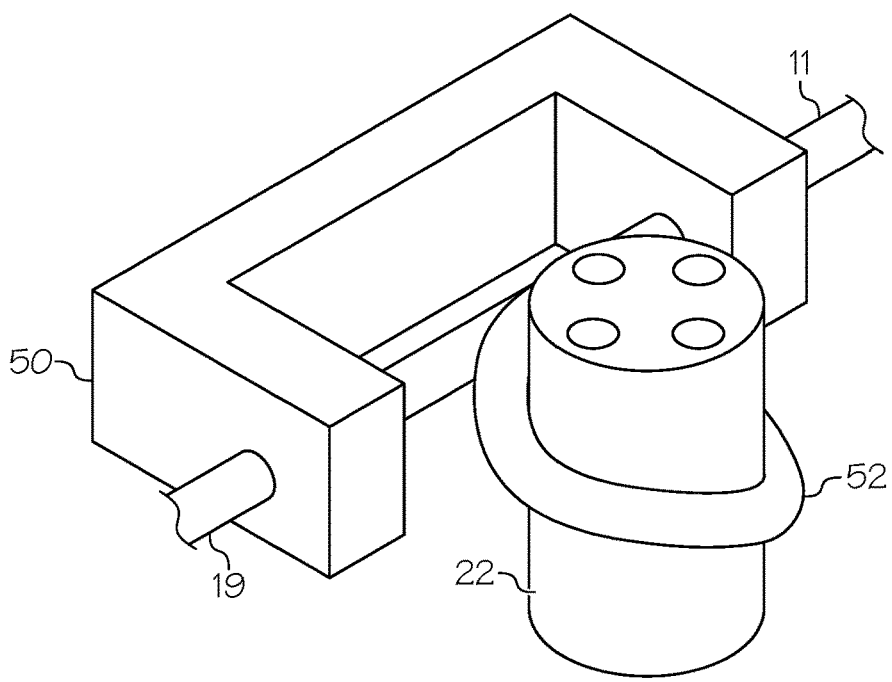

FIGS. 5A and 5B illustrate another cassette embodiment 41 according to the present invention, which is referred to as a pre-kinked "loop" cassette. The pre-kinked loop cassette 41 includes a connector 50 which is similar and/or identical to the connector 30 of FIGS. 1-4, in combination with a segment of pump tubing 51 which includes a loop 52. The loop 52 includes an anti-flow mechanism in the form of a pre-set kink 53, similar and/or identical to kink 33 of FIGS. 1-4, for preventing free flow of fluid when the cassette 41 is not in the receiving portion of the pump. While not shown in FIG. 5A or 5B, the connector 50 of this cassette 41, like connector 30 of FIGS. 1-4, can include a recess with an extending mating member for reversibly connecting to a corresponding pump mating member extending from a recess in the pump housing. As described above for the pre-kinked cassette 21, a mating connection between the two mating members ensures proper alignment of the pump tubing 51 with the pumping mechanism 22 and reversibly locks the loop cassette 41 in place. When desired, the mating members can be disconnected from one another to allow the cassette to be easily removed from the receiving portion of the pump housing.

Prior to actuating the infusion pump 12, the loop 52 of the pump tubing segment 51 is engaged by being manually placed over and tensioned around the rotor 22 by a user. The loop diameter of the pump tubing 51 can be such that the rotor maintains a radial stretch of the looped pump tubing 51, which maintains tension on the kink 53 and thereby permits fluid flow through the cassette 41 upon actuation of the pump. This manual loading of the pump tubing segment 51 of the loop cassette 41 is in contrast to the automatic tensioning/loading of the pump tubing 31 onto the pumping mechanism 22 when using the pre-kinked cassette 21 (see FIG. 3).

Figure 6A:
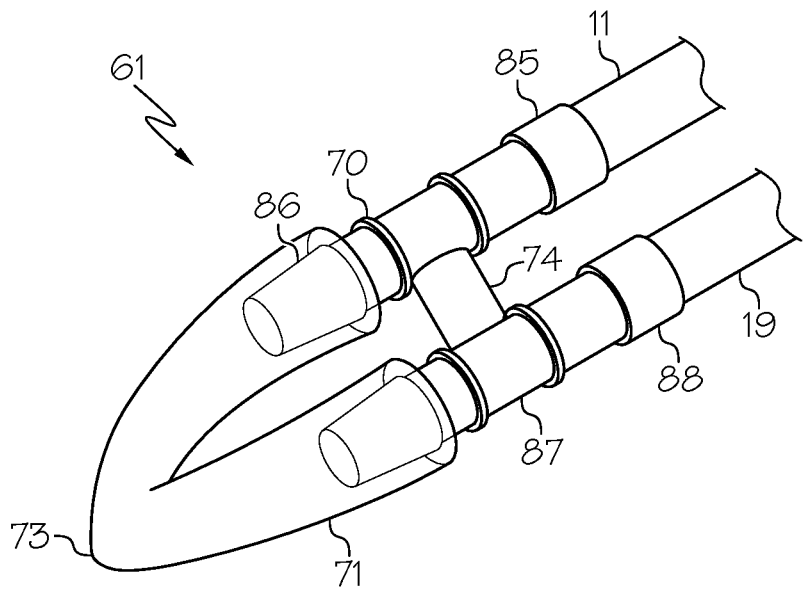
FIGS. 6A and 6B are schematic views of a "simple V-kink" cassette embodiment according to the present invention.
Figure 6B:
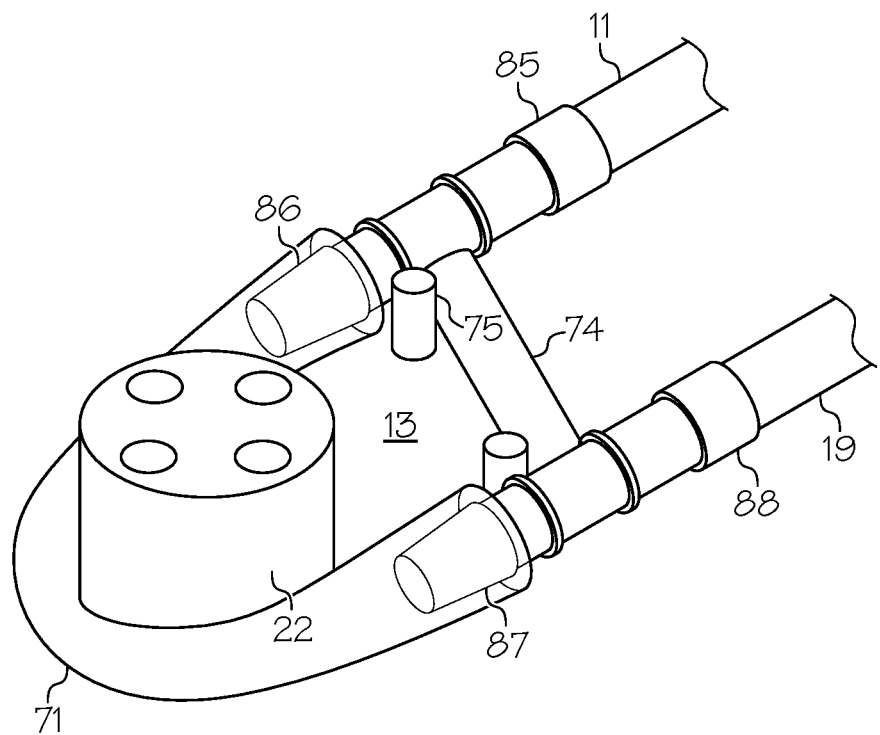

FIGS. 6A and 6B illustrate a "simple V-kink" cassette embodiment 61 according to the present invention, which includes an H-shaped connector 70 and pump tubing segment 71. The pump tubing segment 71 includes a pre-set kink 73, and a pair of free ends which easily and securely attach to a pair of attachment structures 86, 87 at one end of the connector 70. Another pair of attachment structures 85, 88, provide facile and secure attachment of the inflow tubing 11 and outflow tubing 19, respectively. The attachment structures 85-88 are hollow, and have substantially the same size and diameter as the tubing they connect to. Further, attachment structures 85 and 86 are fluidly connected to one another, as are attachment structures 87 and 88, and attachment structures 85, 86 are fluidly connectable to structures 87, 88 via the pump tubing segment 71 of the cassette.

The connector 70 is maintained in position by the reversible connection (as discussed above) of its mating member 74 with the pump housing mating member 75 projecting from the pump housing (not shown). The pump housing mating member 75 can be a pair of brackets, as shown, or it can be in the form of a pair of pins, or a slot. Once the connector 70 is loaded into the pump housing and the pump tubing segment 71 is engaged by being tensioned about the rotor, the distance between the connector's mating member 74 and the rotor 22 maintains tension on the pump tubing segment 71 and thus relieves the obstruction caused by the anti-flow mechanism 73. As can be appreciated from viewing FIG. 6B, the distance between the connector's mating member 74 and the rotor 22 can be such that it maintains tension on the pump tubing 71. More specifically, the length of the pump tubing segment 71 can be such that a radial stretch is placed on the tubing 71 when tensioned around the rotor 22, which stretches the kink 73 and removes the obstruction to fluid flow in the pump tubing. Fluid flow is then permitted through the stretched tubing of the V-kink cassette 61 upon actuation of the pump.

As illustrated, the kinked pump tubing segment 71 prevents free flow of fluid when not engaged with (i.e. stretched by or tensioned about) the pumping mechanism. Like the pre-set kinks 33, 53 of cassettes 21 and 41, the pre-set kink 73 of cassette 61 is located in a tubing segment that, when in use, is not normally straight and/or hanging freely. Unlike prior art hanging segments of tubing that are typically kinked by pinch valves, the kinked pump tubing segment 71 is intended to be stretched upon placement onto the pumping mechanism 22. Such engagement between the pump tubing segment and the pumping mechanism relieves the obstruction caused by the anti-flow mechanism or pre-set kink 73 and allows fluid flow. Like the pre-kinked loop cassette 41, the pump tubing segment 71 of the simple V-kink cassette 61 is manually placed over and tensioned around the rotor 22 by a user prior to actuating the pump.

With cassette 61, loading is quickly and easily performed by the user by first securing the mating member 74 of the connector 70 onto the mating member 75 of the pump housing, and then manually tensioning the pump tubing 71 around the rotor 22. As shown, the mating member 74 may be made of an elastic material capable of being radially stretched to secure the connector to the brackets 75. The pump tubing may be positioned around the rotor first, but typically the user aligns the segment of pump tubing with the rotor while aligning and connecting the mating members. As noted above, once the cassette is loaded, the distance between the housing's mating member 75 and the rotor 22 ensures that the kink 73 is kept in tension and creates no obstruction to flow. Fluid flow is then permitted through the cassette 61, and the motor-driven rotor 22 can be actuated to deliver fluid to the patient.

Figure 7A:
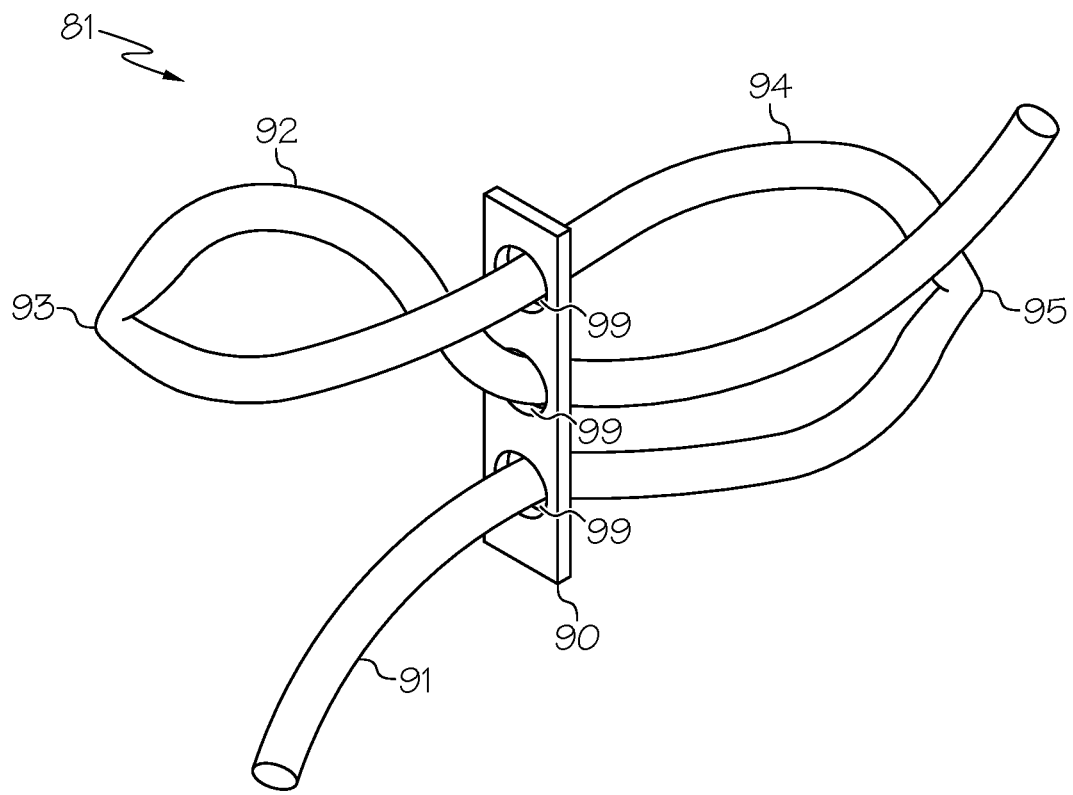
FIGS. 7A and 7B are schematic views of a "dual rotor, kinked figure-8" cassette embodiment according to the present invention.
Figure 7B:
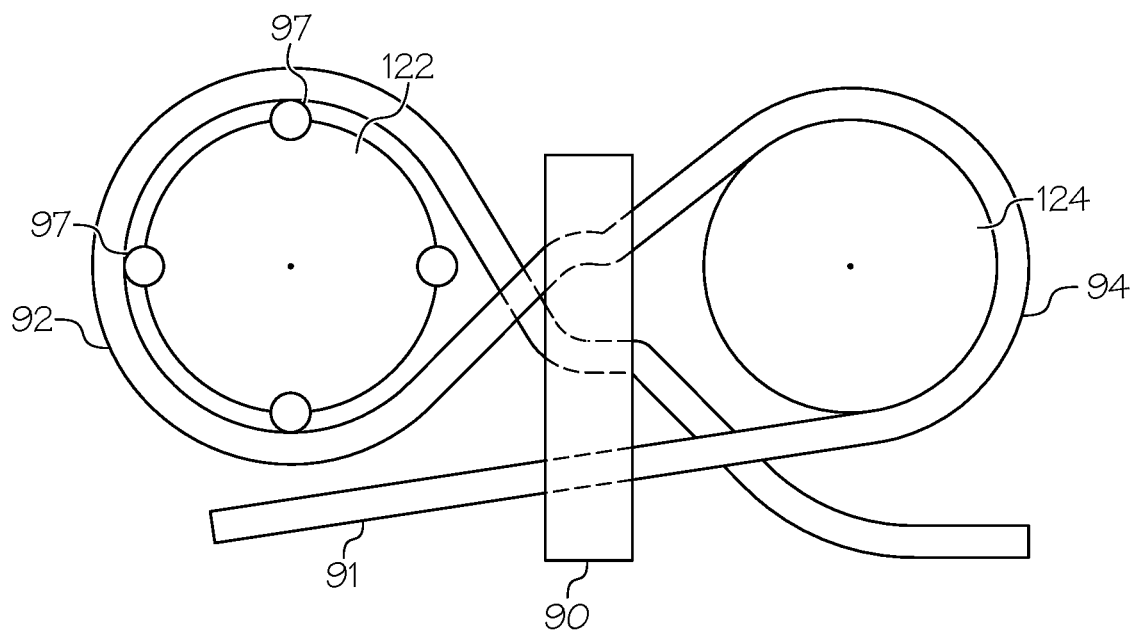

FIGS. 7A and 7B illustrate a "dual rotor, kinked figure-8" cassette embodiment 81 according to the present invention, which is intended for use with infusion pumps with a dual rotary peristaltic pumping mechanism. As shown in FIG. 7A, the cassette 81 includes a connector 90 having three (3) holes 99 for receiving and weaving a single segment of pump tubing 91 therethrough. The pump tubing 91 is inserted into holes 99 of the connector to form two separate kinked loops 92, 94. The connector 90 thus holds the two loops 92, 94 together to provide the shape of a figure-8 on its side. A pair of pre-set kinks 93, 95 in the respective loops 92, 94 restrict flow through the pump tubing 91 when the cassette is not loaded onto the pump, so that the cassette 81 provides an occlusion mechanism to prevent free flow of fluid through the unloaded feeding set.

In use, loop 92 is manually placed over and tensioned around the rotor 122 by a user, while loop 94 is similarly tensioned around the rotating member 124 prior to actuating the pump. The distance between the rotor 122 and rotating member 124 is such that a radial stretch is created, which maintains tension on the looped pump tubing 91, relieving the obstruction caused by the kinks 93, 95. When the cassette 81 is loaded into the dual rotor infusion pump, the two loops 92, 94 are typically manually stretched around the rotor and the rotating member 122, 124, respectively. The rotor 122 includes rollers 97, and functions to peristaltically drive the fluid through the feeding set tubing like a traditional rotary peristaltic pump, while the other rotating member 124 "freewheels" or spins freely, it's only purpose being to keep tension on the loop 94 in order to keep the pump tubing 91 open to flow.

When the kinks 93, 95 are tensioned about their respective rotors 122, 124, fluid flow is permitted through the cassette 81 so that the pump can then be actuated to deliver nutritional fluid to the patient. Also, similar to other connector embodiments described herein, the connector 90 can include a mating member (e.g. 54, see FIGS. 2, 3) for connecting to a corresponding pump mating member (55) extending from the pump housing, such as a button, slot, pins or other feature, to center the connector. Connection of the mating members can ensure proper alignment of the pump tubing 91 within the pumping mechanism for manual loading around the rotors, and can also reversibly lock the cassette in place within the receiving portion of the pump housing. The loaded cassette can then be unlocked and removed from the pump housing by a user, as described above.

Figure 8A:
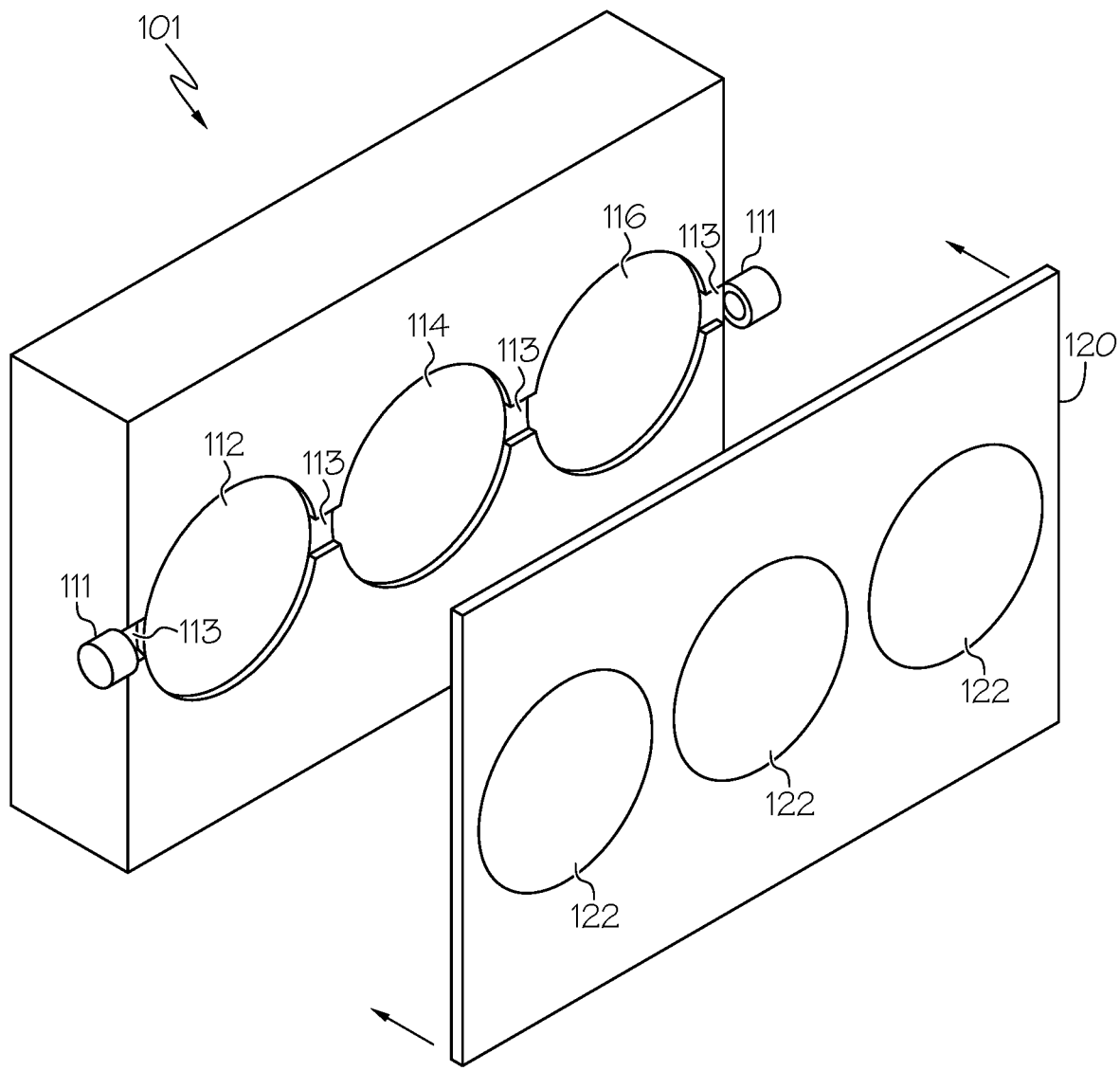
FIGS. 8A and 8B are schematic views of a "3-chamber diaphragm" cassette embodiment according to the present invention.
Figure 8B:
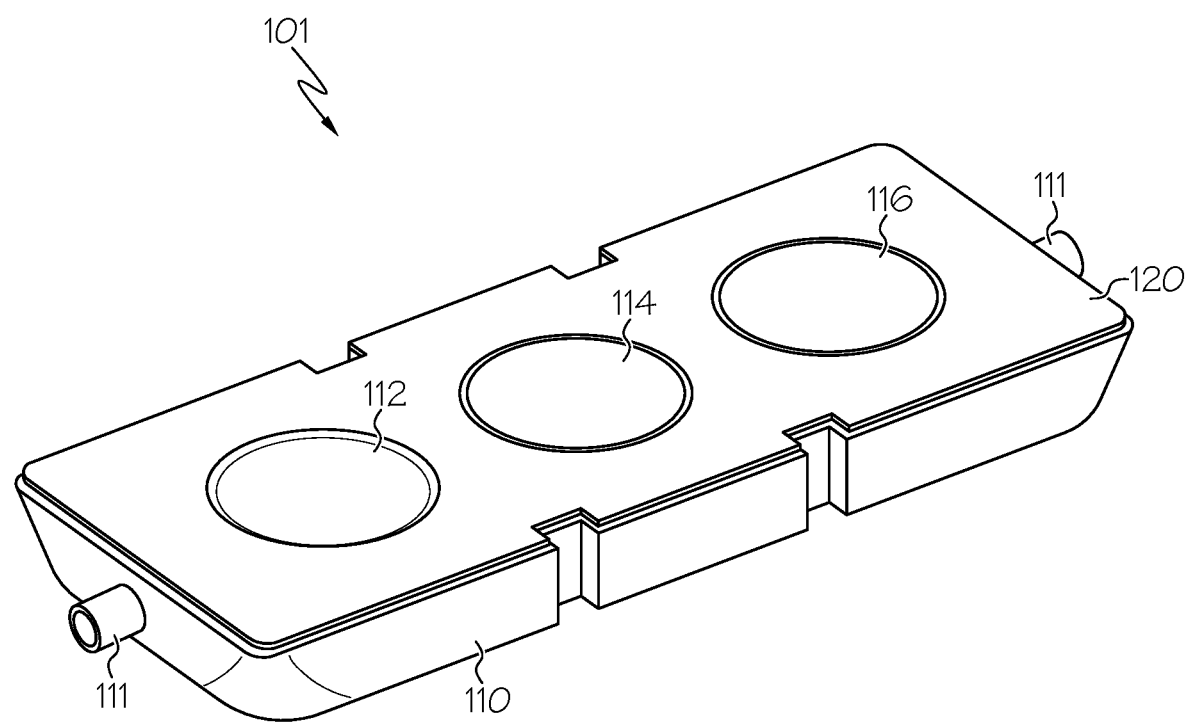

FIGS. 8A and 8B illustrate a "3-chamber diaphragm" cassette embodiment 101 according to the present invention. Cassette 101 includes a connector 110 with three (3) hemispherical chambers 112, 114, 116 and a pump tubing segment 111, and is received within the receiving portion of the infusion pump housing, in a manner similar to the cassettes described above. Also, similar to other connector embodiments described herein, the connector 110 can include a mating member for connecting to a corresponding pump mating member extending from the pump housing, such as a button, slot, pins or other feature. Connection of the mating members ensures proper alignment of the pump tubing 111 within the pumping mechanism, and locks the cassette 101 in place. When needed the cassette can be unlocked and removed from the pump housing, as described above.

Looking at FIG. 8A it is apparent that chambers 112, 114, 116 are separated by passages 113 which constitute a portion of the pump tubing segment 111. To prevent free flow of fluid through the connector 110 when not loaded in the pump, a thin flexible membrane or elastic film 120 is typically sealed around the connector 110 to prevent bulging of the chambers 112, 114, 116 or their passages 113. The diameter of the passages 113 are small in comparison to the chambers 112, 114, 116, and the compressive coating of elastic film 120 can also serve to constrict the passages. Thus, there is no free flow of fluid through the connecting chambers, unless the cassette is loaded onto the pump and one or more of the chambers are compressed by the mechanical fingers of the pumping mechanism. Each of the passages 113 can also include a small check valve or tight opening (not shown) to prevent free flow of fluid therethrough.

In order for fluid to flow through the cassette 101 during operation, the linear pump's array of mechanical fingers must exert a peristaltic force by sequentially contacting, compressing or otherwise occluding the chambers 112, 114, 116 to cause peristaltic flow through the feeding set. More specifically, when the linear pump is actuated, a motor driven rotor causes the mechanical fingers to linearly extend and retract in a wave format to compress the pump tubing segment chambers 112, 114, 116 in a sequential manner, deforming them and creating a pressure wave capable of driving fluid through the passages 113 towards the patient. Release of the cassette from the pump housing removes any external pressure placed on the chambers 112, 114, 116 by the pump's mechanical fingers, and free flow of fluid through the passages 113 is prevented.

In all of the embodiments disclosed herein, the infusion pump can also incorporate an optical reader or sensor, as is known in the art. For example, the optical reader can be in the form of an optoelectronic sensor, essentially, a tiny low-resolution video camera. Such an optical reader can be incorporated into a particular brand of infusion pump and used to recognize that a matching brand of feeding set tubing is being connected to the pump. Specifically, the optical reader can be used to recognize an imprinted item such as a particular trademarked logo (thus matching the trademark/brand of the infusion pump with tubing of the same brand), product number, RFID signal, bar code, or magnetic signature imprinted on the pump set tubing. Thus, the optical eye or sensor on the infusion pump can scan for the presence of the imprinted item on the feeding set tubing (preferably the pump tubing segment, as defined herein), which can confirm that a matching feeding set intended only for use with that type of infusion pump is loaded. The imprinted item can also be used for other functions; for example, depending on the particular item imprinted onto the tubing, a different functionality of the pump could be activated. For instance, one feeding set's tubing can include a particular imprinted item which when read by the optical sensor causes the pump to enter into a calibration mode. In addition, a particular imprinted item can provide wireless connectivity such as electronic medical record (EMR) connectivity to the user, or an imprinted item can indicate a feed and flush mode.

The various embodiments of the invention as illustrated and described above are simpler, easier to use, and are more cost effective than known prior art devices and products. Along with simplicity and ease of use, the inventive cassettes described herein can be relied upon to prevent inadvertent free flow of fluids into the patient. For example, in a prior art pinch valve the tubing made to form a kink is normally straight tubing, and typically requires an elastic member or spring member to put tension on and create a kink in the tubing. Should the spring member become inadvertently dislodged from the tubing, free flow of fluids will result. In contrast, the pre-set kink of the present invention is unique in that the pump tubing does not need to be put under tension to create the kink. Rather, the inventive pump tubing segment is held statically by the cassette, and the tubing must thereafter be stretched, tensioned around, or otherwise caused to engage the rotor/pumping mechanism of the pump before the restriction to flow within the pump tubing is relieved. In addition, the tubing of a prior art pinch valve is not tensioned by the pumping mechanism; rather, prior art pinch valves do not engage, wrap around, contact or otherwise become stretched, tensioned or acted upon by the rotor or pumping mechanism of the infusion pump, nor are prior art pinch valves included as part of a cassette that slides into place within the pump housing.

The inventive cassettes disclosed herein can function as a means to hold a predetermined length of pump tubing for reliably and reversibly engaging the pumping mechanism. By locking the cassette into the pump, the feeding set/pump circuit can be completed. While specifically intended for delivery of enteral fluids, the embodiments of the present invention disclosed herein may be suitable for use in many applications that involve peristaltic pumping systems generally, and can be particularly beneficial for delivery of parenteral fluids. The embodiments disclosed herein thus may be modified to accommodate many types of feeding sets and the like that are suitable for use in healthcare facilities as well as in home care environments. Such feeding sets may be adapted with various types of tubing to accommodate a variety of enterally deliverable liquid nutritional products which may have various viscosities and consistencies.

While particular embodiments of the present invention have been illustrated and described herein in considerable detail, the details regarding these embodiments are not intended to restrict or limit the scope of the appended claims. Accordingly, while only a few such embodiments are particularly described and illustrated herein, it should be understood that the practice of additional modifications and variations of these embodiments, and the equivalents thereof, are within the scope of the invention as recited in the following claims.

What is claimed is:

1. A V-kink cassette for use with enteral nutritional fluid infusion pumps having a rotary peristaltic pumping mechanism, the cassette comprising:
   a) a pump tubing segment for engaging a single rotary pumping mechanism located within a peristaltic infusion pump, wherein the pump tubing segment comprises a pre-set kink and a pair of free ends, and wherein the pre-set kink presents an obstruction to free flow of fluid when not engaged with the pumping mechanism; and
   b) an H-shaped connector for engaging the pump tubing segment with the pumping mechanism, the H-shaped connector comprising a connector mating member, a first pair of attachment structures, and a second pair of attachment structures, wherein the first pair of attachment structures connect to the pair of free ends of the pump tubing segment, and wherein the second pair of attachment structures connect to inflow tubing and outflow tubing of a nutritional feeding set passing through the infusion pump.

2. The V-kink cassette of claim 1, wherein the connector mating member reversibly engages a pump housing mating member projecting from the infusion pump to align the pump tubing segment with the pumping mechanism and to lock the cassette in place within the infusion pump.

3. The V-kink cassette of claim 2, wherein engagement of the connector mating member with the pump housing mating member tensions the pump tubing segment about the pumping mechanism and relieves the obstruction caused by the pre-set kink.

* * * * *